US006755384B2

(12) United States Patent
Gorfain

(10) Patent No.: US 6,755,384 B2
(45) Date of Patent: Jun. 29, 2004

(54) FLEXIBLE PLATFORM FOR LIQUID HANDLING ROBOTS

(75) Inventor: Elliott Gorfain, Huntington Beach, CA (US)

(73) Assignees: Hitachi Chemical Co., Ltd. (JP); Hitachi Chemical Research Center, Inc., Irvine, CA (US)

( * ) Notice: Subject to any disclaimer, the term of this patent is extended or adjusted under 35 U.S.C. 154(b) by 69 days.

(21) Appl. No.: 10/127,077

(22) Filed: Apr. 18, 2002

(65) Prior Publication Data

US 2002/0190178 A1 Dec. 19, 2002

Related U.S. Application Data

(60) Provisional application No. 60/284,464, filed on Apr. 18, 2001, and provisional application No. 60/301,679, filed on Jun. 27, 2001.

(51) Int. Cl.[7] ............................................. F16M 13/00
(52) U.S. Cl. .................. 248/618; 248/678; 248/646.01
(58) Field of Search .................. 248/346.2, 346.03, 248/346.04, 346.01, 678, 581, 618, 560

(56) References Cited

U.S. PATENT DOCUMENTS

| | | | |
|---|---|---|---|
| 1,350,970 A | * | 8/1920 | Hutchison et al. ..... 248/346.03 |
| 4,309,912 A | | 1/1982 | Smith |
| 4,330,386 A | | 5/1982 | Korinek et al. |
| 4,399,362 A | | 8/1983 | Cormier et al. |
| 4,522,454 A | * | 6/1985 | Hochstatter .................. 384/26 |
| 4,676,656 A | | 6/1987 | Cook et al. |
| 5,785,926 A | | 7/1998 | Seubert et al. ............... 422/100 |
| 5,922,604 A | | 7/1999 | Stapleton et al. ............. 436/46 |
| 5,927,547 A | | 7/1999 | Papen et al. .................. 222/57 |
| 6,079,283 A | | 6/2000 | Papen et al. ............. 73/864.11 |
| 6,083,762 A | | 7/2000 | Papen et al. ................ 436/180 |
| 6,094,966 A | | 8/2000 | Papen et al. ................ 73/1.74 |
| 6,112,605 A | | 9/2000 | Papen et al. ............. 73/864.22 |
| 6,203,759 B1 | | 3/2001 | Pelc et al. ................... 422/100 |
| 6,220,075 B1 | | 4/2001 | Papen et al. ................ 73/1.74 |
| 6,449,893 B2 | * | 9/2002 | Spinner ....................... 42/127 |

FOREIGN PATENT DOCUMENTS

| | | | | |
|---|---|---|---|---|
| EP | 0190019 | | 8/1986 | |
| JP | 2125120 A | * | 5/1990 | ................ 248/560 |

* cited by examiner

Primary Examiner—Ramon O. Ramirez
(74) Attorney, Agent, or Firm—Knobbe, Martens, Olson & Bear, LLP

(57) ABSTRACT

A flexible platform or plate holder for use with liquid handling robots. More specifically a flexible platform for use with a variety of plate holders which allows for complete removal of a sample from a well without the need for liquid sensors.

24 Claims, 15 Drawing Sheets

FLEXIBLE PLATFORM FOR LIQUID HANDLING ROBOTS

This application claims priority under 35 U.S.C.§119(e) of U.S. Provisional applications Ser. No. 60/284,464, filed Apr. 18, 2001, and 60/301,679, filed Jun. 27, 2001, both of which are incorporated by reference in their entireties.

FIELD OF THE INVENTION

The invention relates to a flexible platform or plate holder for use with liquid handling robots. More specifically the invention relates to a flexible platform for use with a variety of plate holders which allows for complete removal of a sample from a well without the need for liquid sensors and for the addition of small volumes without creating bubbles.

BACKGROUND OF THE INVENTION

Liquid handling robots are the cornerstones of modern automated biological laboratories. Yet, while they make some tasks much easier to accomplish than manual methods, there are still some tasks that are beyond the capabilities of current instrumentation. Most of these limitations involve processes that normally require the sensitive touch of a human being. For example, such processes include the ability to manipulate the tip of a pipetman to the bottom of a tube or well and to extract all or nearly all of the liquid within that tube. Another example is the ability to add a small volume of liquid to a tube or well without creating a bubble or bubbles. This is very important in biological reactions, as they are typically carried out in a very small volume, typically in the range of 1–100 $\mu$l, but with an increasing trend towards even smaller volumes in the nanoliter and picoliter range. Under these conditions, bubbles or any variance in the concentration of the components can lead to detrimental results. Thus, if the sample is involved in a number of different reactions within the same tube or well of a plate, it is important to include a washing step and a drying step. The final drying step should ideally eliminate all residual volume in the well, so that the next reaction is not diluted. One can imagine that if a typical reaction occurs in a total volume of 20 $\mu$l and 5 $\mu$l are left after the previous step, this is a significant contaminant or dilution.

Current instrumentation is very precise, but not flexible. Thus, current robots cannot account for slight plate-to-plate size or shape variations or even well-to-well size or shape variations within a plate. Variation in the seating of disposable pipette tips on the liquid handler can also pose positional problems for the robot. Although robots can be programmed such that the arm will go to an exact fixed location in space, they cannot be programmed to go to the bottom of a well, particularly if there is variation in the distance. In addition, with current automation, there is no way to apply a controlled amount of pressure between the robot arm and a plate. So, if one tries to program the robot arm to go to the bottom of a well and aspirate, it may leave a residual volume at the bottom of the well if the tip is too high (which can vary tremendously in the context of the small total volumes involved), or it may collide the tips of the robot into the bottom of the well which may damage the experiment and/or the robot (and prevent aspiration).

Various methods and apparati have been envisioned or developed as alternative solutions to this problem. For example, pipet tips which include liquid sensors have been developed. However, these tips are very expensive and may necessitate the purchase of one or more further apparati for allowing the detection. In addition, these sensing tips do not work reproducibly with small volumes. An alternative is to make the arm of the liquid handler flexible. However, this may require each manufacturer to separately re-engineer the arm of the machine, a very expensive process.

Thus a method is needed which is inexpensive and will allow for a means of controlling for variations in the height of wells or plates and will be applicable to a variety of automated handlers from different manufacturers.

SUMMARY OF THE INVENTION

One embodiment of the present invention is a platform for a liquid-handling robot having at least one robot nozzle for transferring or treating a liquid sample in a sample holder by moving upward and downward, the platform having a sample platform for receiving the sample holder; an adapter platform for fitting onto the liquid-handling robot; and a moveable connector elastically connecting the sample platform and the adapter platform, wherein elasticity of the connector is adjusted to be lower than the force of the downward movement of the nozzle to elastically lower the sample platform when the nozzle pushes the sample holder downward.

In one embodiment, the platform is configured to receive sample holders such as microtiter plates, PCR plates, microarrays, and microfluidic plates.

In a further embodiment, the platform also has chamfers for attachment of the sample holder. In a further embodiment, the platform also has a bumper between the sample platform and the adapter platform to prevent contacting each other.

In one embodiment, the moveable connector has at least one coil spring and at least one support arranged within the coil spring. Typically the support is selected from the group consisting of a screw, a pin, a nail, and a rod.

In a further embodiment, the platform also has a washer.

In a further embodiment, the sample platform and/or the adapter is manufactured of a material which is chemically inert and thermally resistant, such as a plastic.

In one embodiment, the sample platform has at least one adapter pin for positioning the adapter platform in the liquid handling robot.

A further embodiment is a platform for a liquid-handling robot having (i) a detachable sample holder having at least one well or groove for a liquid sample; (ii) an adapter for receiving the platform; and (iii) at least one robot nozzle for transferring or treating the sample in the well by moving upward and downward, the platform having: (a) an upper surface configured to contact a bottom of the sample holder, (b) a bottom surface configured to contact an upper surface of the adapter, and (c) a mechanism elastically moveable in a direction of movement of the nozzle, wherein elasticity of said platform is adjusted to be lower than the force of the downward movement of the nozzle. In one embodiment of the sample platform, the upper surface of the platform is configured to receive a sample holder selected from the group consisting of microtiter plates, PCR plates, microarrays, and microfluidic plates.

In a further embodiment, the upper surface of the platform is an upper surface of a sample platform, the bottom surface of the platform is a bottom surface of an adapter platform, and the moveable mechanism is constituted between the sample platform and the adapter platform. The moveable mechanism may be a connector and a spring. And the connector may be a screw, a pin, a nail, and a rod.

In a further embodiment, the platform also has at least one bumper for preventing the sample platform and the adapter platform from contacting each other.

A further embodiment is a method for adapting an automated liquid handler, by attaching the platform described above to an automated liquid handler to allow for variations in plate and well-size.

A further embodiment is a method for the complete aspiration of small volumes by a liquid plate handler, comprising attaching the platform described above to an automated liquid handler.

A further embodiment is a method for transfer of small volumes by an automated liquid handler, comprising attaching the platform of claim 1 to an automated liquid handler.

A further embodiment is a method for perfecting the function of microarray spotters, comprising attaching the platform of claim 1 to an automated liquid handler.

A further embodiment is a platform for any type of liquid handling robot, which has a sample platform; an adaptor platform which fits onto the liquid handling robots; and a moveable connector which allows motion on one axis between the two platforms.

In one embodiment, the sample platform allows for attachment of a sample adapter. In a further embodiment, the sample platform allows attachment of a sample holder selected from the group consisting of: microwell plates, pcr plates, microarrays, and microfluidic plates. The platform may also contain chamfers for attachment of a sample holder. In a further embodiment, the platform may contain a bumper to keep the sample platform from contacting the adaptor platform. The movable connector may be a connector and a spring. The connector may be a screw, a pin, a nail, or a rod, preferably a shoulder screw.

In one embodiment, the sample platform and or adaptor is manufactured of a material which is inert. In a further embodiment, the sample platform further comprises helicoils to allow for better attachment of the screws or pins.

BRIEF DESCRIPTION OF THE DRAWINGS

Various features aspects and advantages of the present invention will now be described with reference to the drawings of the preferred embodiment, which embodiment is intended to illustrate and not to limit the invention, and in which:

FIG. 7a is a drawing of the base plate and top plate and FIG. 7b is a drawing of the recessed holes 75 to be drilled into the thicker (base) plate 3.

FIG. 8a shows the flexion of the platform.

DETAILED DESCRIPTION OF THE PREFERRED EMBODIMENT

Figure 1A:
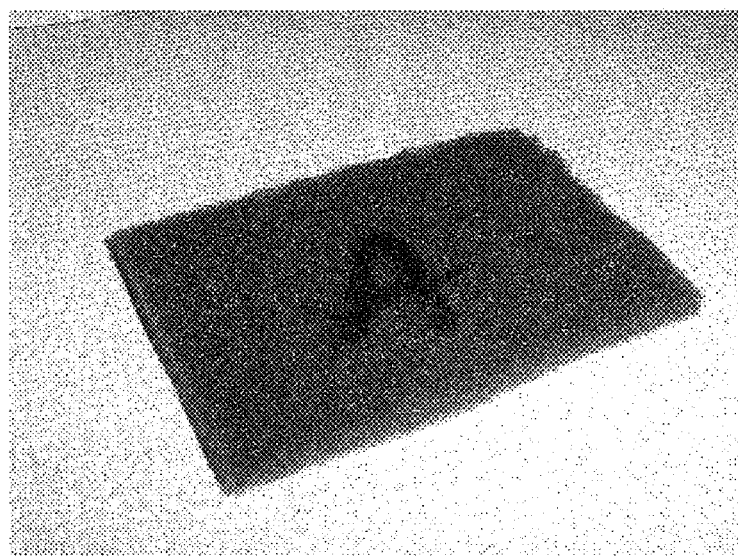
FIG. 1a–d illustrates a number of prototypes of the preferred embodiment which illustrates the evolution from a simple type of flexible platform to one which is more complex.

The device and variations described herein provide a flexible platform device for use with a robotic liquid handling system such as those typically found in an automated biotechnology laboratory. The platform can be used to support and align various microtiter plates or the equivalent as the liquid handling robot is manipulating them. The platform does this by providing a limited amount of pressure between the disposable tips of the liquid handler's pipettor and the bottom of the wells of a microtiter plate. The purpose for the resistance is to allow the tips to touch the bottom of the well, but not to press so hard as to damage the machine, the disposable tips, or the microtiter plate and not so hard as to stop the aspiration or dispensing of the pipettor. The platform will not provide so much pressure as to make a complete seal between the tip and the microtiter plate, but it will apply enough force that the microtiter plate itself may flex a little under the pressure from the robot. This technique will allow the liquid handler to be programmed to remove all of the liquid from the wells of the microtiter plate without damaging the plate, tips or machine or leaving residual liquid in the wells of the plate. In other words, this will allow the liquid handler to aspirate a plate or well to dryness. This should be the case even if the microtiter plate is warped or if there is variance between plates.

The current state of laboratory automation relies heavily upon robotic liquid handlers to accurately dispense and aspirate small volumes of liquids to and from microtiter plates. An important aspect of these manipulations is the interface between the pipette tip and the microtiter plate.

When dispensing small volumes into a plate, it is important that the pipette tip be accurately positioned within the well. The tip cannot be too far above the well bottom, nor can it come in contact with the well bottom. If the tip is too high, the fluid may not be released into the well (it may be retained on the tip), the fluid may cling to the side of the well, or bubbles may become trapped beneath the fluid at the bottom of the well. In contrast, if the tip is too low and it touches the plate, a pressure seal will form, preventing dispensing and possibly damaging the tip and or the plate.

When aspirating small volumes from a plate, it is also important that the pipette tip be accurately positioned within the well. The tip must not be above the fluid level in the well, nor can it contact the well bottom. If the tip is above the fluid level, the fluid will not be aspirated and air will be aspirated instead. If, while aspirating, the tip comes in contact with the bottom of the plate, a vacuum seal will occur between the tip and the plate, and the fluid will not be aspirated. The lower the volume in the plate, the more difficult it is to accurately and reproducibly place the pipette tip in the proper position. Thus, the most difficult aspiration to achieve is a complete aspiration of fluid from a well within a microtiter plate.

What complicates pipette tip positioning even more is that there is a variance in both the positioning of the wells in the microtiter plate and the positioning of the disposable tips on the liquid handler. The positional variance of the microtiter plate wells can be up to 1 mm (much greater if the plate has undergone thermocycling), and the positional variance of the disposable tips (depending on the liquid handler) can be from 0.5 to 2 mm.

There have been many attempts to solve this crucial problem, but none of the solutions thus far have addressed all of the issues satisfactorily. Most instrument-based attempts have focused on either flattening the plate out with a "claw" (or vacuum) or using liquid level sensing tips to sense fluid levels. While the "claw" approach does flatten out the plate, the wells within the plate are often still out of alignment, and the claw does nothing about the positional variance of the pipette tips. On the other hand, liquid level sensing tips are not very reliable, are expensive, and have constraints that prohibit it from working with low volumes.

The flexible platform herein was designed to overcome the problems associated with low volume aspiration and dispensing on robotic liquid handlers. The device also makes it much easier to write protocols for liquid handlers and results in procedures that have a higher level of reproducibility. The device is a flexible platform for robotic liquid handlers that holds microtiter plates and allows for tip-to-plate contact while preventing a vacuum or pressure seal. This allows for faster protocol development by increasing the functional range for tip placement and results in a very high level of reproducibility.

For example, a typical technique that frequently uses a robotic liquid handling platform and is often automated is that of poly(A)+mRNA purification and reverse transcription polymerase chain reaction (PCR). During the process the following steps occur: 1. Hybridize total RNA, 2. Wash and aspirate to dryness, 3. Reverse transcribe, 4. Wash and aspirate to dryness, 5. PCR, 6. Wash and aspirate to dryness, and 7. More PCR. A typical PCR reaction occurs in approximately 10–1001 µl, the washes are typically in a larger volume, so it is clear that with the number of steps that are occurring in the same well, if 5–10 µl are left after aspiration, the results of the PCR could be radically altered, particularly considering the sensitivity of the assay.

SUMMARY OF A TYPICAL FLEXIBLE PLATFORM

With reference initially to FIG. 1, a variety of embodiments of the flexible platform is illustrated. The flexible platform may be of two types. A simple prototype is constructed of a single layer of flexible material such as foam. FIGS. 1a, b, and c provides examples of such a prototype. A second type, such as the one in FIGS. 1d and 2, involves two layers, designated as the top plate 2 and the base plate 3. With reference to FIG. 2, this type of flexible platform contains some type of resistance mechanism, such as a spring and may also contain a joining mechanism, such as a pin 9, which keeps the spring 1 from overextending after compression. The prototype shown in FIGS. 11–16 is configured to be used with the BIOMEK 2000 liquid handler, so it is an example of a prototype specifically designed to fit a specific machine. However, in a further embodiment, a universal flexible platform may include the embodiment of FIGS. 11–16 with the following differences: the top plate may include flanges to allow for secure attachment of a sample holder, such as a microtiter plate. The bottom plate may contain no special adaptations, such that it may be used with any liquid handler. Further variations of the flexible platform will be described with reference to the drawings and examples.

In one embodiment, the actual dimensions and materials used to construct the flexible platform can vary as long as the ability to align the plate and provide upward pressure is not compromised. The flexible platform may posses general dimensions which may afford the platform the ability to either sit on top of a device known as a "labware holder", or to replace a labware holder. These labware holders are designed to align a microtiter plate while a liquid handling robot is manipulating it and thus the flexible platform of the invention may also allow for this manipulation. However, unlike the labware holders, the flexible platform allows for a limited amount of upward resistance against the microtiter plate.

In a further embodiment the general dimensions of all of these devices may be any dimension which fits a labware holder or automated platform. In one embodiment, the dimensions are from about 2 mm to 200 mm long by 2 mm to 200 mm wide by 05 mm to 50 mm high or less. In a further embodiment the dimensions may be approximately 125 mm to 140 mm long by 80 mm to 108 mm wide by 5 mm to 40 mm high or a size which fits under or on the "labware holder" and keeps the chamfers free to set the microtiter plate stably upon the "labware holder" or flexible platform. Some options for the device could include adjustable height and/or adjustable resistance.

Detail of Base Plate

Figure 5:
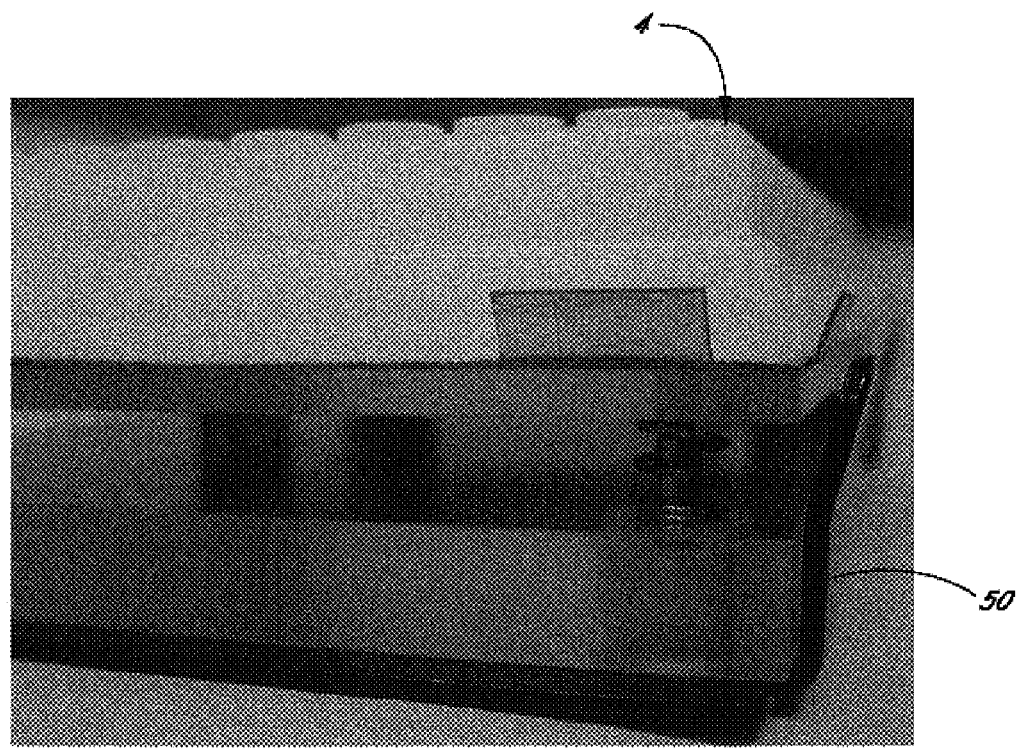
FIG. 5 is a side view of the flexible platform of FIGS. 3 and 4 showing the insertion of the platform into a labware holder 50 and a microtiter plate 4 inserted on top within the chamfers 10.

The base plate 3 (see FIG. 2 for an example) of the flexible platform of the preferred embodiment has two main variations. The first version has a base that is designed to be placed on top of a labware holder (see FIGS. 1a–e, and 2 ). This version may have design specifications that may allow the base to fit snugly on top of the labware holder (see FIG. 5). The embodiments shown in FIGS. 1 and 2 are examples of this type. The second version may have a base that is designed to fit directly onto the deck of the liquid handler, and may replace a labware holder. The embodiment shown as FIGS. 8 and 9 are an example of this type. This version could have aligmnent pins placed on the bottom that may snap into the same holes that the labware holder normally utilizes to keep itself in place.

Both base versions could be manufactured from metal (sheet or cast) or a variety of polymers that could have various degrees of flexibility.

Detail of Top Plate

With reference to FIG. 2, the top plate 2 of the flexible platform may have essentially the same specifications as the top of a labware holder. That is, it may be flat, and may have alignment tabs 10 around the edge (also called chamfers) that may align a variety of multi-well plates that conform to standards set up by the Society for Bimolecular Screening (SBS). The top plate 2 and the chamfers 10 could be manufactured from metal (sheet or cast) or a variety of polymers selected on the basis of durability and flexibility.

Detail of the Resistance Mechanism

With further reference to FIG. 2, the resistance mechanism 1 is located between the top plate 2 and the bottom plate 3 of the flexible platform. Although in the Embodiment in which the flexible plate holder is constructed of a single piece of foam (FIGS. 1*a–c*), the resistance mechanism is the material it is constructed of. There are a variety of different methods that can be employed. The main goal is to provide a constant resistive force when pressure is applied from above. Some methods of achieving this are as follows: a foam pad (FIG. 1*a*), a multiple spring assembly (FIG. 2), an air cushion, or magnets. For the foam pad, a variety of different foams could be employed that may be selected on the basis of their resiliency and durability. For the spring assembly, the same factors may apply. The springs could be standard coiled, conical coiled (these provide a lower spring rate which may deliver a more constant force) or even flat springs. The air cushion could be a static air cushion or a regulated pressure air cushion that is supported by an air compressor. The air compressor version could be regulated to convey various different resistances to the plate holder. The air cushion may likely be in a bladder. Finally magnetic repulsion could be employed by putting magnets of the same polarity on the underside of the top plate and on the topside of the base plate. However, this last version could pose some problems with the robot's circuitry.

Detail of the Joining Mechanism

With reference to FIG. 2, in the embodiment which has a top plate 2 and a base plate 3, a tether 9 is used in order to hold the top plate 2 and the base plate 3 together. This tether 9 could be any attachment known to one of skill in the art such as a flexible wire, a pin, or an adjustable screw. The tether has three main purposes: First, to hold the top plate 2 and the base plate 3 together and to secure the resistance mechanism 1 in place; Second, to keep the top plate 2 at a maximum height so that one side does not overextend when downward pressure is applied to the opposite side of the top plate; Third, a screw based joining mechanism 9 may allow for a height adjustment of the space between the plates. In addition, a screw based joining mechanism may also allow for the easy replacement of the resistance mechanism should it wear out over time and need replacement. Or, if one required different degrees of resistance then one could have multiple sets of resistance mechanisms with different resistances that could be easily interchanged within a single device.

Summary of Variables

In summary, it can be envisioned that the flexible platform can be constructed to fit on top of the labware holder, for example, recessed so that the microtiter plate is still held securely by the chamfers in the labware holder (ie: a foam pad). In this case, the microtiter plate may sit on top of the foam pad. Alternatively, the flexible platform can be constructed to replace the labware holder completely, in which case the top plate may mimic the top of the labware holder and may hold a microtiter plate securely, and the base plate may mimic the base of the labware holder and may fit securely onto the deck of the liquid handling robot. A further embodiment of the flexible platform could be constructed such that the platform is simply an adapter that fits between the labware holder and the deck of the liquid handler (with the top surface of the top plate mimicking the deck of the liquid handler, and the bottom surface of the bottom plate mimicking the bottom of the labware holder). Alternatively, the flexible platform could be constructed to fit on top of a labware holder, but would also have its own alignment tabs, or chamfers, on the top of the top plate for aligning the microtiter plate. Thus, a flexible platform can be produced which may be usable on any type of liquid handling robot, or the flexible platform could be produced to specifically fit onto a specific manufacturer's liquid handling robot.

Examples of some of the above embodiments will be described as follows:

Summary of Prototypes

Figure 2:
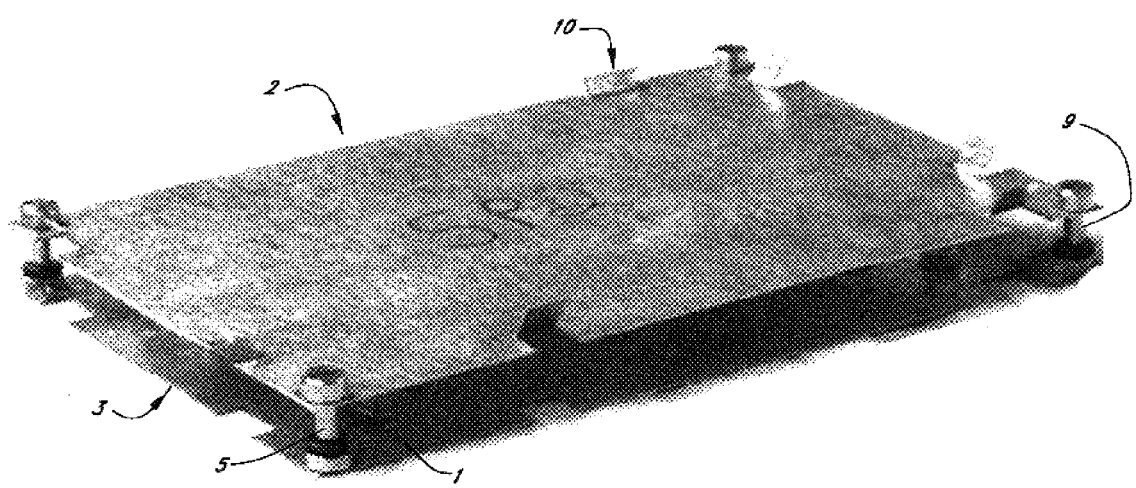
FIG. 2 is an isometric view of the flexible platform in 2 showing the top plate with chamfers 10 to hold the plate in place, and the base plate 3 which may contain the necessary attachment devices for attaching to the platform of the liquid handling robot.

1) Flexible Platform Prototype A (see FIG. 1*a*)

Cut from "eggcrate" foam this mechanism was very rough. The prototype was constructed of a foam resistance mechanism and was designed to sit on a specialized labware holder (for tip boxes—it had higher alignment tabs). The alignment tabs of the labware holder extended beyond the foam and were used to align the plate. The foam had a moderate resistance.

Figure 1B:
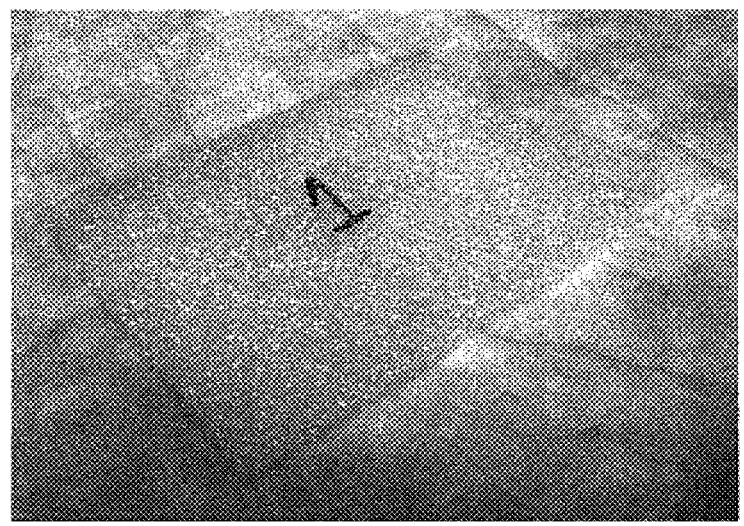

2) Flexible Platform Prototype 1 (see FIG. 1*b*)

Cut from packing foam of a constant thickness this prototype was of a high resistance. The prototype was constructed of a foam resistance mechanism and was designed to sit on a specialized labware holder (for tip boxes—it had higher alignment tabs). The alignment tabs of the labware holder extended beyond the foam and were used to align the plate. This prototype was tested with very good results for aspirating to dryness, however, because it did not have alignment tabs, the plate moved around on the pad too much for consistent results. The range of volumes left in the wells was 0 to 0.9 ul. The average was 0.294 ul (see Example 1 for the method of testing).

Figure 1C:
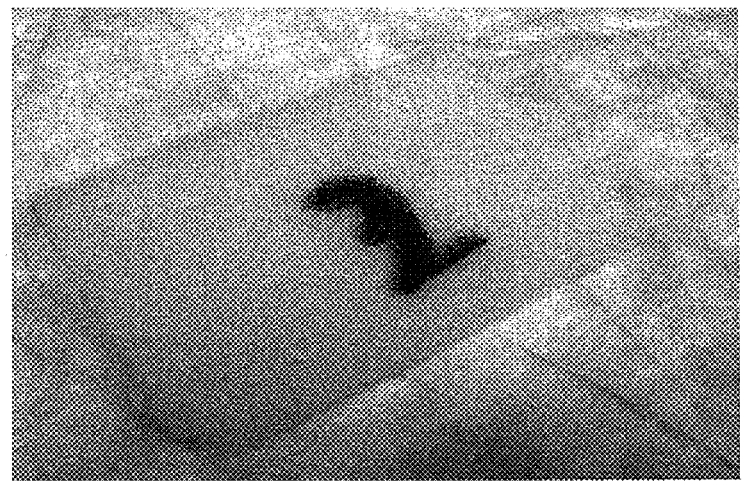
Figure 1D:
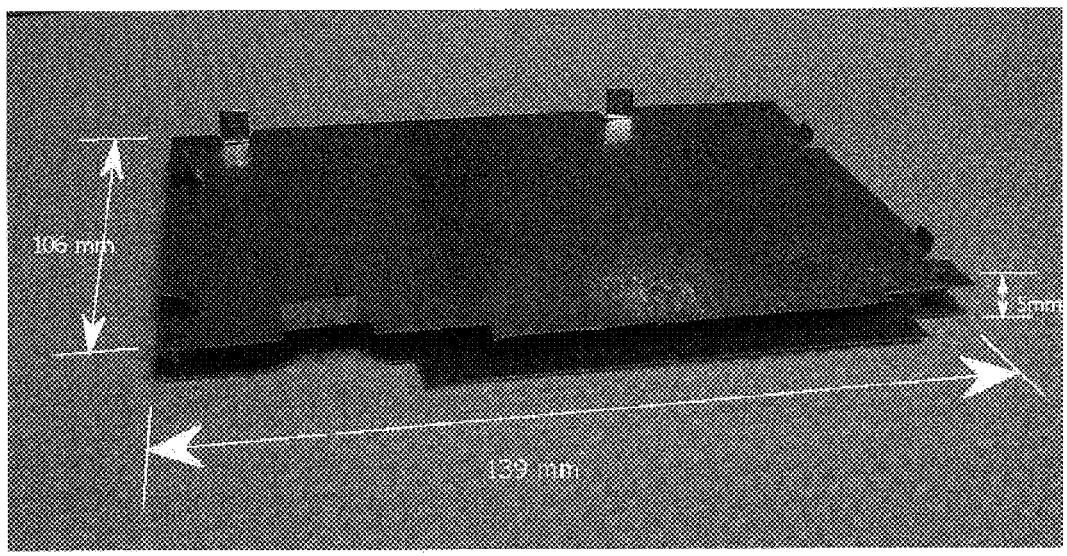

3) Flexible Platform Prototype 2 (see FIG. 1*c*)

Cut from packing foam of a constant thickness this prototype was of a low resistance. The prototype consisted of the foam resistance mechanism and was designed to sit on a specialized labware holder (for tip boxes—it had higher alignment tabs). The alignment tabs of the labware holder extended beyond the foam and were used to align the plate. This prototype was tested with very good results for aspirating to dryness, but in order to provide more consistent results, the plate needed to be held onto the pad. This prototype worked almost exactly the same as prototype "1". The range of volumes left in the wells was 0 to 0.9 ul. The average was 0.284 ul.

4) Flexible Platform Prototype SP1 (see FIGS. 1*c* and *d* as well as FIG. 2)

Sheet metal top and base plate with spring assembly resistance mechanism: This prototype was the first one that incorporated many of the components listed above. The top 2 and base plate 3 were manufactured from sheet metal. The base plate design was one that mounted on top of a standard labware holder. The top plate design 2 was a mimic of the top of the labware holder. The resistance mechanism was a spring assembly 1, and the joining mechanism used the pin method 5. The spring resistance was moderate. In functional tests this model outperformed the foam-type prototypes, leaving so little residual volume that conventional measuring techniques could not be used. The range of volumes left in the wells was 0 to ~0.4 ul. The average was ~0.2 ul.

5). Flexible Platform Universal Prototype I (see FIGS. 3–5)

In this prototype the pins 1 were on the bottom and recessed 20 such that the platform could fit any liquid handler. The flexible platform could be made up of any material such as acrylic or metal. The top plate 2 had chamfers 10 or some method of stably holding the microtiter plate 4.

6). Flexible Platform Prototype 2 (see FIGS. 8 and 9)

In this prototype, although the pins 1 were on the bottom and recessed 20 as in the universal prototype I, the top plate 2 allowed attachment of a labware holder 50. For example, the Beckman labware holder attached to the top plate and the whole apparatus fit onto the platform of the Beckman liquid handler. The base plate 3 may be made to fit within the labware holder or may simple fit onto the liquid handler. Alternatively, the base plate may be designed such that it fits onto a specific liquid handler.

7). Nonuniversal Adapter

The flexible platform is made to be completely universal and an adapter is made which allows it to fit into a specific brand or type of machine. Examples of liquid handler manufacturers include PACKARD, BECKMAN, GILSON, TECAN, ZYMARK, TOMTEC, PROTEDYNE, LABMAN, ROSYS, and TITAN. Examples of some manufacturers that make washers that could also use the flexible platform of the invention include BIO-TEK and TITER-TEK.

One embodiment of the flexible platform configured in accordance with the preferred embodiments will now be described with reference to FIGS. 10–16.

Figure 10:
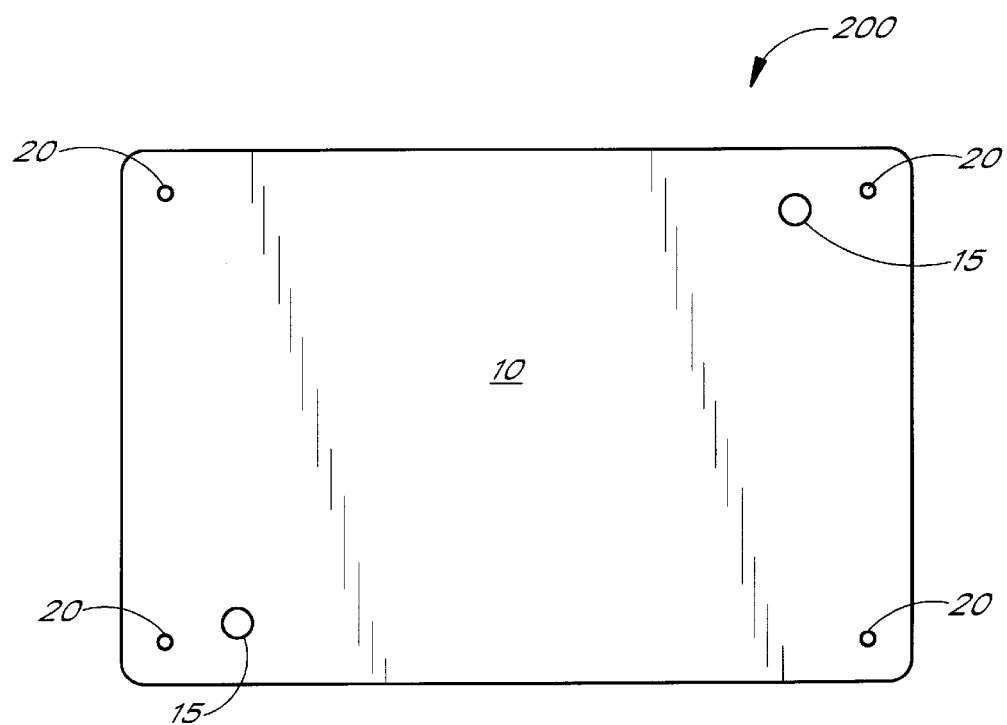
FIG. 10 is a top view of the flexible platform of a preferred embodiment.
Figure 11:
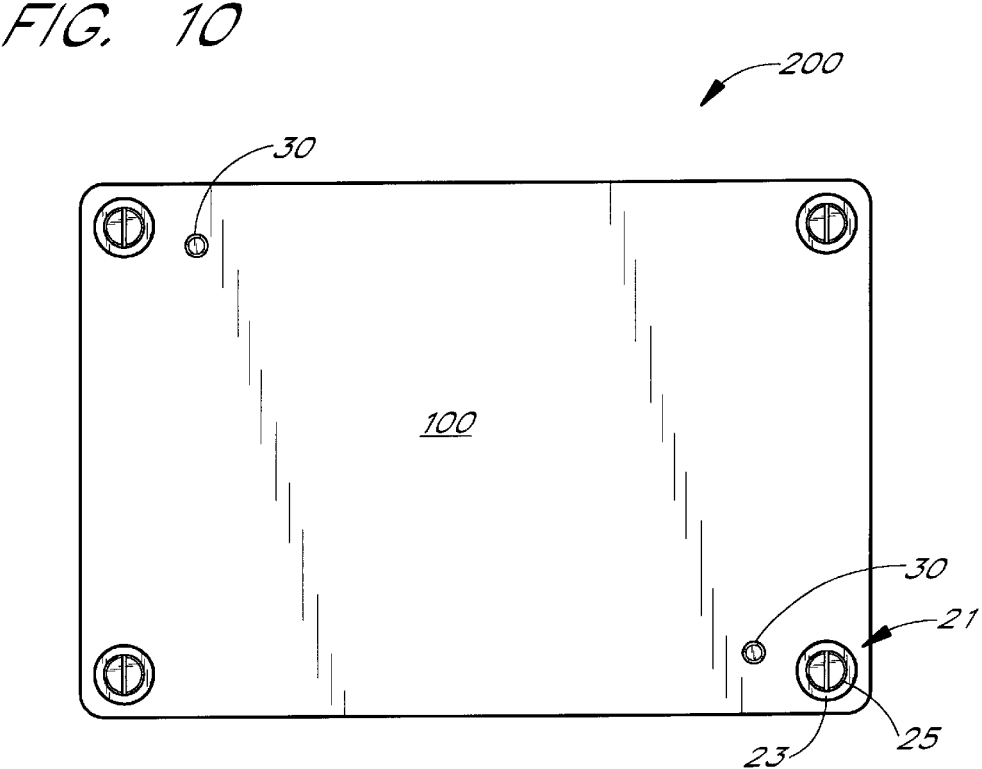
FIG. 11 is a bottom view of the flexible platform of a preferred embodiment.

In FIG. 10, a top view of the flexible platform configured in accordance with the preferred embodiments is shown which is specifically designed to fit the BIOMEK 2000 sample holder and FIG. 11 is a bottom view of the flexible platform which is designed to attach to a BIOMEK 2000 liquid handler platform. The top view shows the top plate 10 of the attachment for the labware holder. This includes two labware (sample) holder attachment holes 15 which allow for the attachment of the BIOMEK 2000 sample holder. The labware holder attachment holes 15 are of a size which allows attachment securely enough that the sample holder will not move laterally. Too much lateral motion may interfere with correct positioning of the samples. The top plate 10 also contains a number of attachments for the flexible connector 70 (these holes contain threaded metal inserts, or heli-coils, with a 4/40 thread. A shoulder screw 25 is inserted into these heli-coils).

In FIG. 11, a bottom view of the flexible platform configured in accordance with the preferred embodiments is shown which is specifically designed to fit the BIOMEK 2000 liquid handling platform. The bottom plate 100 contains four attachment devices 70 with heads 25 for a flexible connector 60, which also, in this embodiment, serve to attach the top plate 10 and the bottom plate 100 together. The head 25 of the attachment devices 70 are shown recessed. The bottom plate 100 also contains pins 30 for attachment to the deck of the liquid handling robot. These pins 30 may be any type of pin known to one of skill in the art, including, but not limited to: any type of detente pin, screw, plain metal pin and/or plastic pin. The pins may be inserted using any method known to one of skill in the art, including but not limited to: screwing the pins in (if they have threads), pressure insertion, gluing, and molding the pins of the same material as the bottom plate 100. The pins 30 may additionally be of any shape known to one of skill in the art, including but not limited to sharp, flat, including protuberances for a tighter fit, slightly tapered to allow ease of insertion, and rounded.

The bottom plate 100 is attached to the top plate 10 by flexible connectors 60. The flexible connectors 60 are composed of an attachment device 70 with a head 25 and a spring 75 (see FIG. 12). The recessed flexible connectors 60 may be produced by any method known to one skilled in the art. However, in the embodiment shown in FIG. 11, the flexible connector 60, comprises an attachment device (70) with a head 25 which is recessed below the bottom surface of the bottom plate 100, producing a recess 21 with a rim 23. Having the flexible connector 60 recessed ensures that it will not interfere with attachment of the flexible platform 200 to the platform of the liquid handler. The size of the recess 21 may be as deep or as wide as necessary to provide room for the head 25 of the flexible connector 60, while still allowing for removal and attachment of the flexible connector 60. Thus, the recessed rim 23 of the recess 21 may be of any size which still allows removal of the attachment devices 70. The attachment devices 70 may be any type known to one of skill in the art, including but not limited to a shoulder screw nail, a screw, a peg, a hook, etc. and may be removable or non-removable. If the attachment device 70 is removable, preferably, the head 25 contains an adaptation which allows for the use of a phillips or regular screw driver or any other tool known to one of skill in the art.

Figure 12:
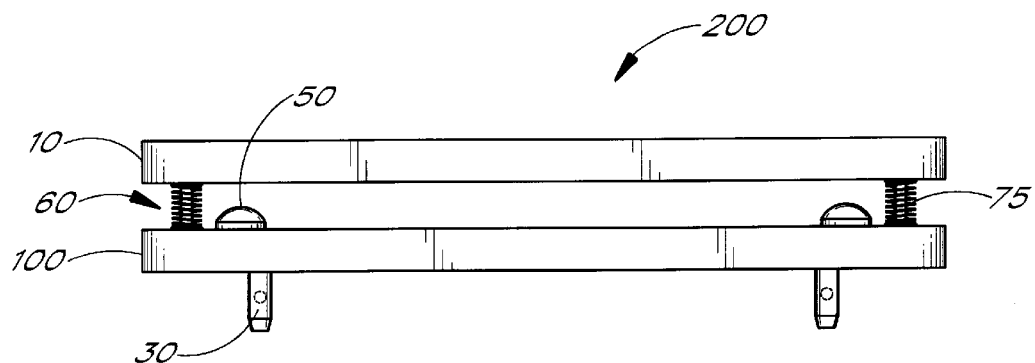
FIG. 12 is a front view of the flexible platform of a preferred embodiment.
Figure 13:
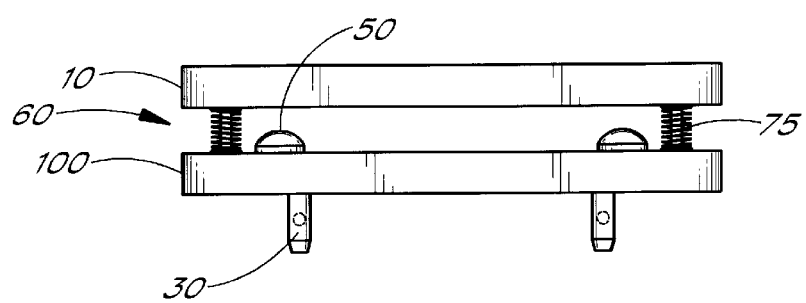
FIG. 13 is the right side view of the flexible platform of a preferred embodiment
Figures 14, 15:
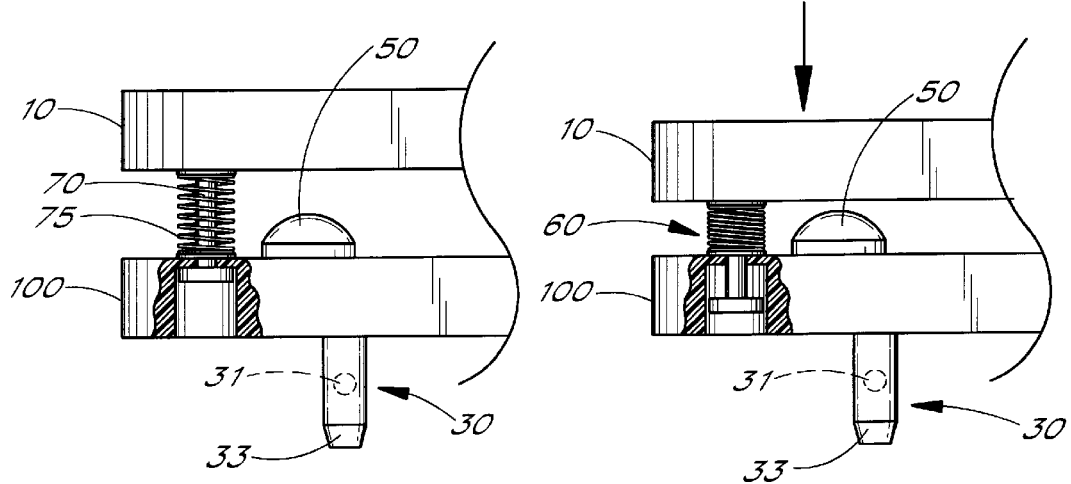
FIG. 14 is a close-up view of the flexible connector of the flexible platform of a preferred embodiment showing the resting configuration.
FIG. 15 is a close up view of the flexible connector of the flexible platform of a preferred embodiment showing the configuration when activated.

With further reference to FIGS. 12 and 13, this embodiment of the flexible platform 200 will be further described. FIG. 12 and 13 show a side and front view of the platform. The flexible connector 60 can be seen to comprise two parts, the attachment device 70 with a head 25, and a spring 75. The spring 75 may allow an amount of play or movement by the connector such that, if necessary, it allows movement on one axis between the two plates (10 and 100). Thus, in FIG. 14, the spring 75 is in the resting position in which no force is being applied to it. In FIG. 15, a force has been applied to the top plate 10 which causes the spring 75 to retract. At the same time, the head 25 of the attachment device 70 moves within the recess 21 toward the bottom surface of the bottom plate 100. In this embodiment, the attachment device 70 is a shoulder screw.

It can be seen by one of skill in the art, that the flexible connector 60 may be envisioned in a further embodiment to be oppositely produced so that the recess is in the top plate 10 and the force causes the attachment device 70 to move toward the surface of the top plate 10.

However, in either case the movement of the spring 75 and attachment device 70 allows for "play" or flexibility of the flexible platform 200 such that movement may occur in one plane. The movement, results in the distance between the two plates decreasing in response to a force.

The spring 75 may be any spring known to one of skill in the art and may depend upon the material which is used to manufacture the plate. For example, a heavier material may require a spring 75 with more tension, while a lighter material may require a spring 75 with less tension.

In the embodiment shown in FIGS. 11–16, the flexible platform 200 has four flexible connectors 60. However, other embodiments may contain one flexible connector 60 which may be envisioned to be positioned in the middle of the device. Alternatively, the platform 200 may only need two flexible connectors, three flexible connectors or may have up to 20 flexible connectors. The flexible connectors 60 may be positioned anywhere on the device which would allow for movement without interfering with proper functioning.

Although not necessary for proper functioning of the flexible platform 200, at least one bumper may be included which in FIGS. 12–15 may be identified by the number 50. The bumper 50 may be made of any material known to one of skill in the art. However, preferably the bumper 50 is of a material which stops the movement of the plates before the spring is fully compressed to its "solid height" (so as not to damage the spring), but is not so hard that it damages the plates. At the same time, the bumper 50 is preferably manufactured of a material which is not so flexible that it does not return to its previous shape and size. In other embodiments, the flexible platform 200 may include 2 bumpers, three bumpers, four bumpers, and even more as necessary, depending on the types of forces which may be applied.

With reference to FIGS. 14 and 15, the pin 30 which allows for attachment to the BIOMEK 2000 liquid handler platform may be seen. In the embodiment shown in FIGS. 14 and 15, the pin 30 includes a protuberance 31 which allows for a tighter fit between the liquid handler platform and the flexible platform 200 of the preferred embodiment. The pin 30 also contains a tapered portion 33 which allows for easier attachment. In the case of the BIOMEK 2000 two pins are needed for attachment at opposite corners of the device. However, one of skill in the art could envision alternative adaptors containing different numbers and types of pins which could be specifically designed to fit other liquid handler platforms.

Figure 16:
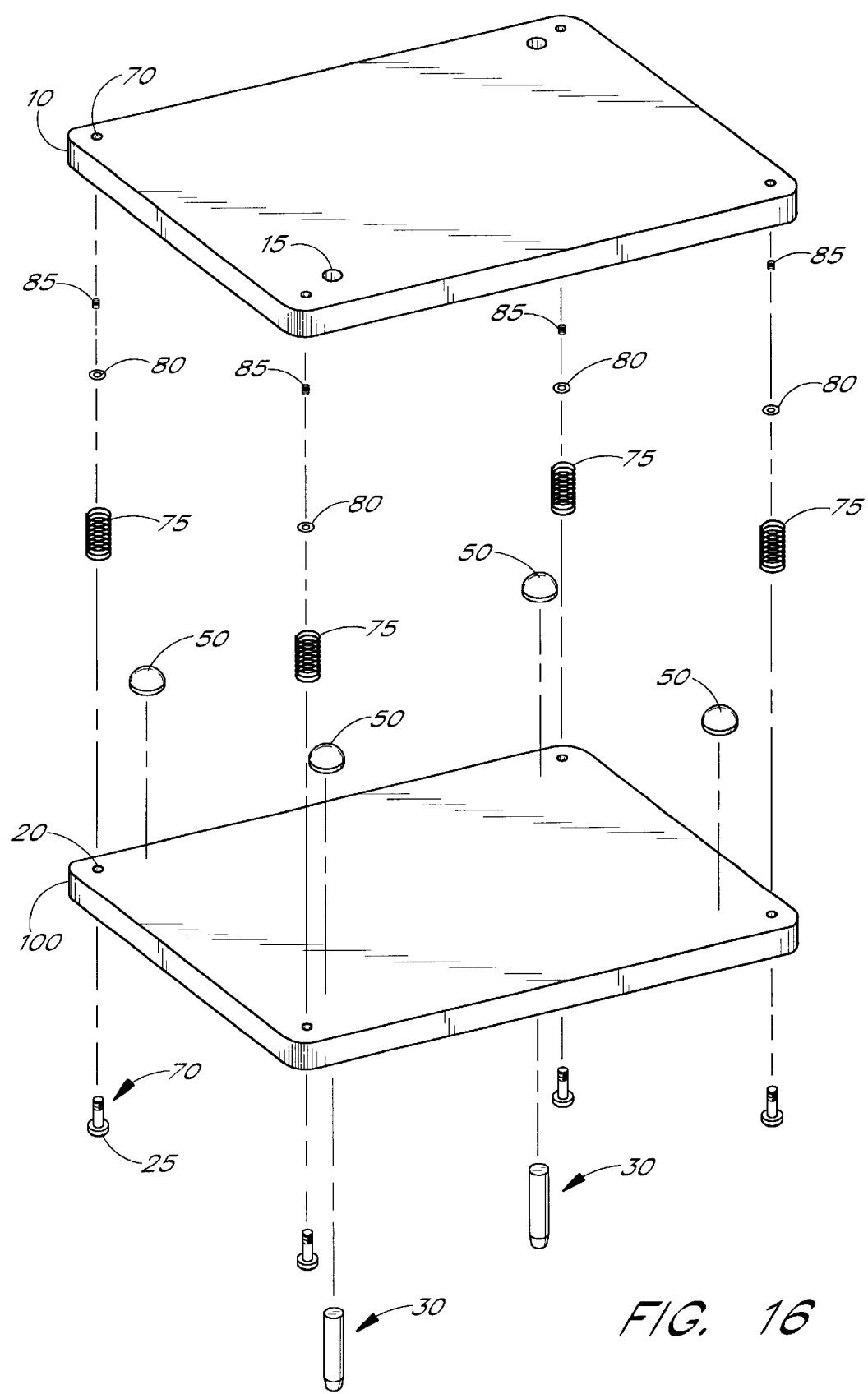
FIG. 16 is an exploded view of the flexible platform of a preferred embodiment.

FIG. 16 provides an exploded view of the flexible platform 200 which shows the attachment of the top plate 10 to the bottom plate 100 by way of the flexible connectors 60. In this view it can be seen that washers 80 may be included to allow the attachment devices 70 to be more firmly seated in the material of the bottom plate 100. This is particularly advantageous when the material is a softer material than that of the attachment devices 70. In addition, helicoils 85 may be included to allow better seating of the attachment devices 70 into the material.

Use of the Universal Prototype 2

The use and making of the prototype 2 will now be described with reference to FIGS. 8a, 8b and 9.

Figure 8A:
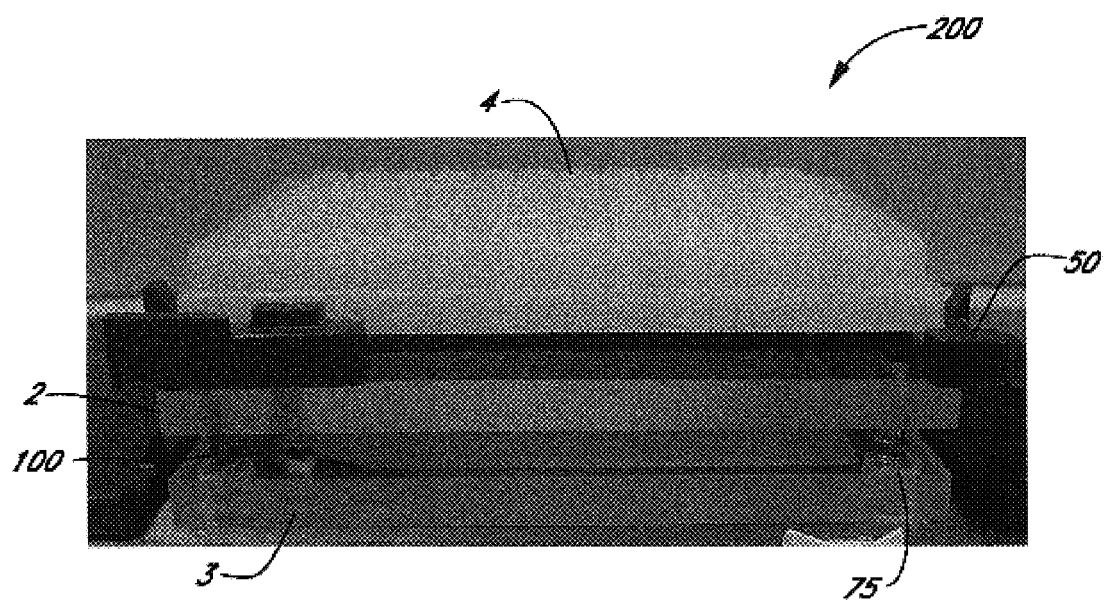
FIGS. 8a and b is a side view of a flexible platform which allows the attachment of the labware holder 50 onto the top plate 2 of the flexible platform and which fits onto the platform of the liquid handler.
Figure 8B:
Figure 9:
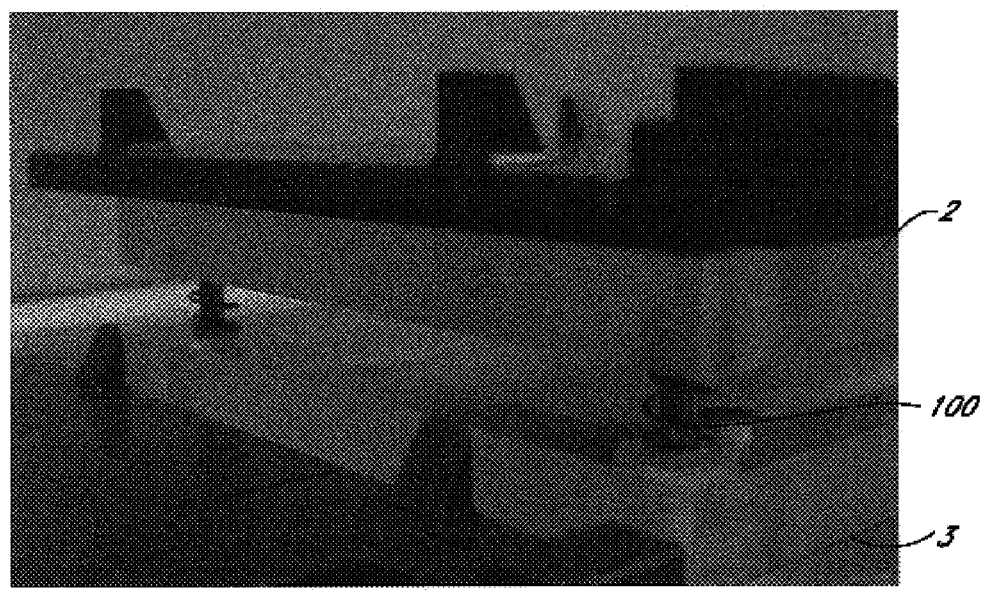
FIG. 9 is an isometric view of the corner and side of the flexible platform of FIG. 8 showing the combined spring and pin 100 which is recessed into the base plate 3.

In FIG. 8a, the universal prototype 2 of the flexible platform is pictured. The flexible platform is constructed of two plates in a stacked conformation attached in a secure but flexible manner. The universal prototype 2 comprises a top plate 2 and a base plate 3, both constructed of acrylic. The construction of the plates is as in Example 2. The bottom plate contains a recessed hole 75 which contains the pin and resistance mechanism (combined spring and pin 100). The combined spring and pin 100 are securely attached to the top plate 2. A labware holder 50 is securely attached to the top plate 2. A multi-welled plate 4 sets onto the labware holder 50. The flexible platform with labware holder attached is placed onto the deck of the liquid handling robot 200. In this example, the top plate of the flexible platform contains attachment sites for the labware holder 50. However, it can be envisioned that the flexible platform may not require specialized attachment sites for the labware holder 50 if it can sit securely on top of the flexible platform without them. It is also envisioned that the base plate 3 may contain a specialized attachment for the platform of the liquid handling robot. With reference to FIGS. 8a and b, as the arm of the liquid handling robot adds liquid or removes liquid from the wells of the multi-welled plate 4, there may be variation in the size or height of the wells. Therefore, the arm is set to touch the bottom of the multi-welled plate, but if the bottom of one of the wells varies, the flexible platform will flex (see FIG. 8b in which the platform is being flexed by the force of a finger). This allows for a more precise removal and addition of liquid.

An alternative example of the Universal prototype will be described with reference to FIGS. 10-16. It can be envisioned that a further embodiment of the Universal Prototype may be produced similarly to the BIOMEK 2000 adaptation, without the specific adaptors. For example, the pins 30 used to attach the flexible platform of FIGS. 10–16 may be removed or alternatively, the plate may be manufactured without pins 30. Thus, in order to fit securely on the platform of the liquid handling robot, the flexible platform 200 may include a friction device or universal attachment device, such as an adhesive. Alternatively, the flexible platform may not need a device and may sit on the liquid handling platform (alternatively on the labware holder itself) in such a way that it will not be easily moved or unseated. Further, the attachment holes 15, which allow attachment to a sample platform may be removed and replaced with flanges or comparable devices which allow a microtiter (96-well) plate or other type of sample device to be securely, but not permanently attached. The method used to attach the sample may vary depending on the use for the liquid handling device and the type of sample holder. For example, flanges might be used to hold a 96 well plate, while pins might be used to hold a PCR plate. Alternatively, if the robot is being used to apply samples to a microarray, an alternative attachment may be used which allows for secure attachment of microarray slides (ie: a clip).

In an alternative embodiment, the universal adaptor may fit on top of the liquid handler platform and a holder is designed to fit on top for each specific sample holder. The holder may be made out of a plastic or similar material and may fit on top. The holder may contain for example chamfers to fit a 100 well plate.

The flexible platform of the preferred embodiments will now be described with reference to the following examples which are meant to illustrate the device and not to narrow it.

EXAMPLES

The following examples show the advantages of the flexible platform and provide an example of the construction of an embodiment of the flexible platform. Example 1 provides an experiment in which residual liquid was monitored after removal using various embodiments of the flexible platform and no flexible platform as a control.

Example 1

Residual Liquid Test

Figure 6:
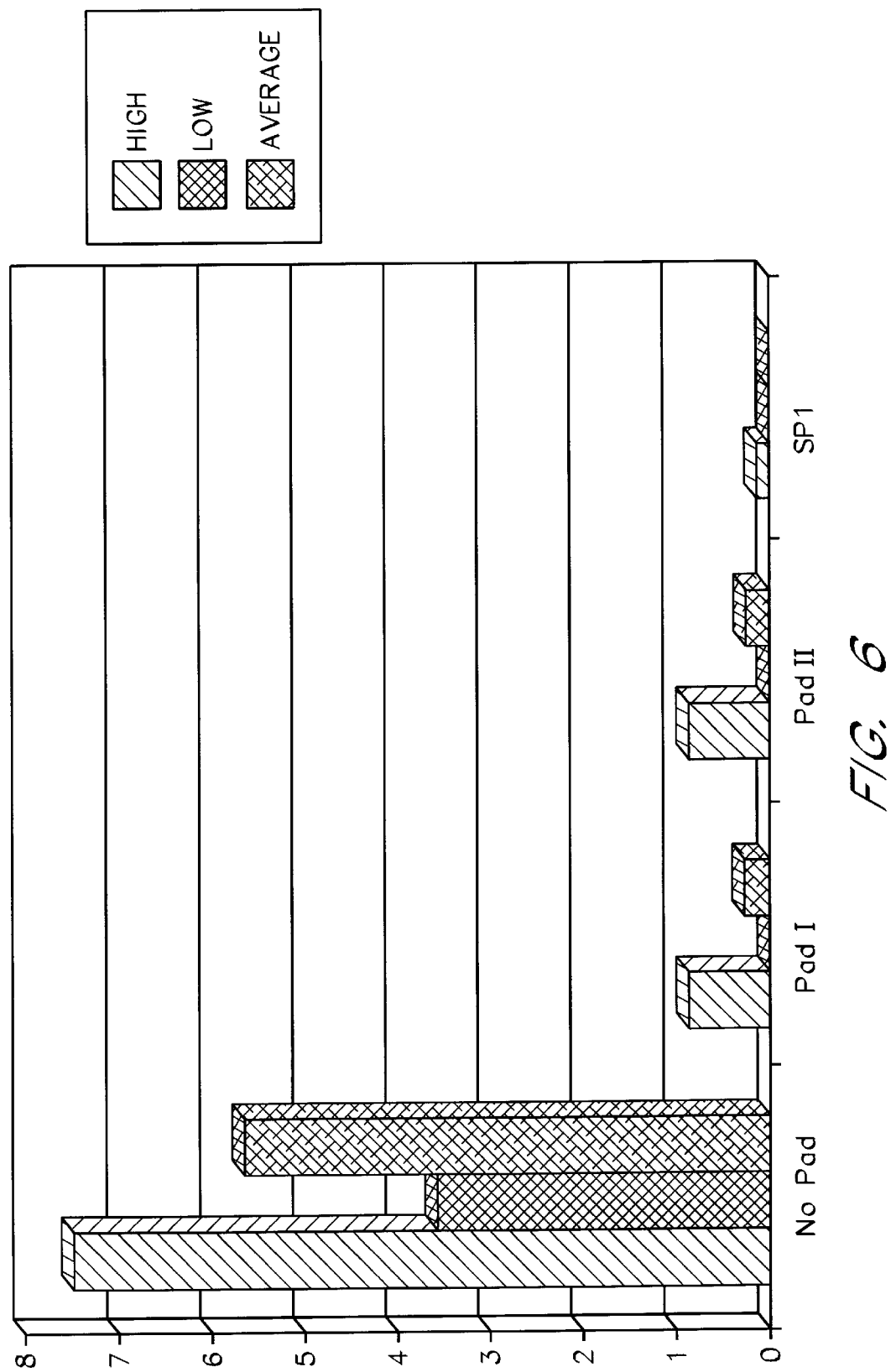
FIG. 6 is a graph showing the results of a trial experiment comparing the residual liquid left using no pad, (Pad I) the pad shown in FIG. 1b, (PadII) the pad shown in FIG. 1c, and SP1—the flexible platform shown in FIG. 1d.

Prototypes of the flexible platform of the preferred embodiments were tested in a Beckman Bio 2000 Liquid Handler for residual liquid after aspiration. Various volumes of liquid were placed into the wells of a microtiter plate. Then the amount of liquid which was left after aspiration was analyzed. The amount left was identified as High, Low, and Average. FIG. 6 shows the results of the test which was a dramatic decrease in the amount of liquid left in the wells after aspiration when using the flexible platform. The prototypes tested were as follows: Lane 1=no pad, Lane 2=(Pad I) the pad shown in FIG. 1b, Lane 3=(PadII) the pad shown in FIG. 1c, and lane 4=SP1—the flexible platform shown in FIG. 1d.

Example 2

Construction of the Universal Prototype

Figure 3A:
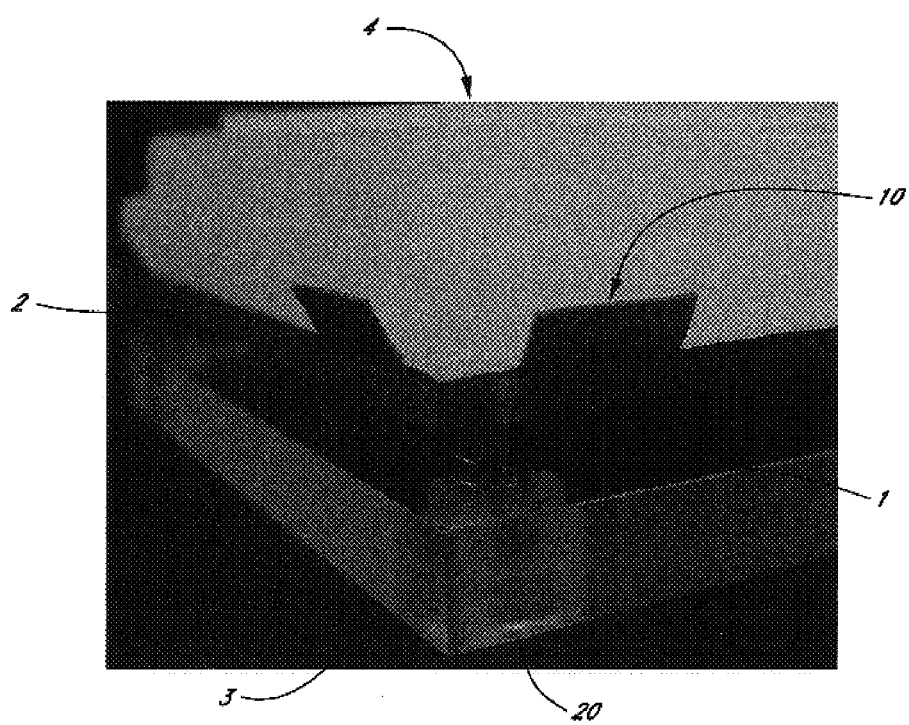
FIGS. 3a and b are isometric views of the corner of a preferred embodiment of the flexible platform made of acrylic, showing a multi-welled plate 4 placed on the top plate within the chamfers 10.
Figure 3B:
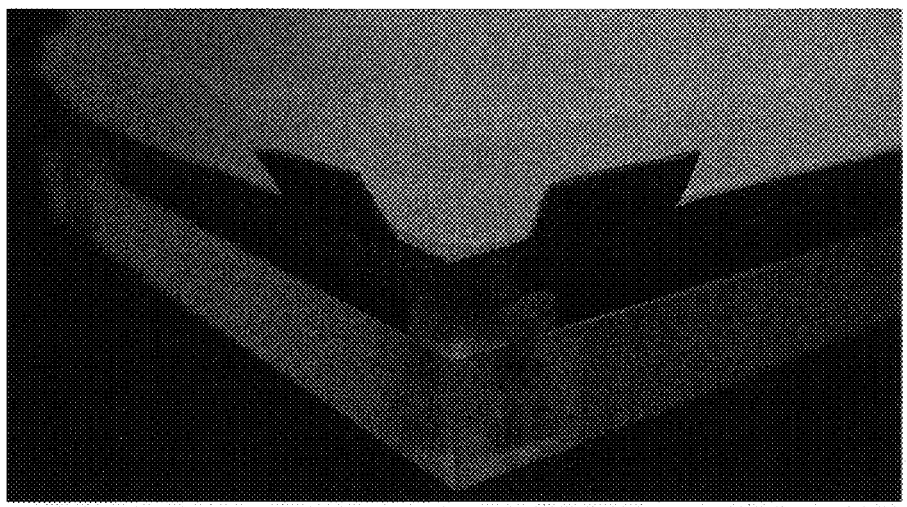
FIG. 3b shows the flexible platform when a force is placed on top allowing flexion of the spring mechanism.
Figure 4:
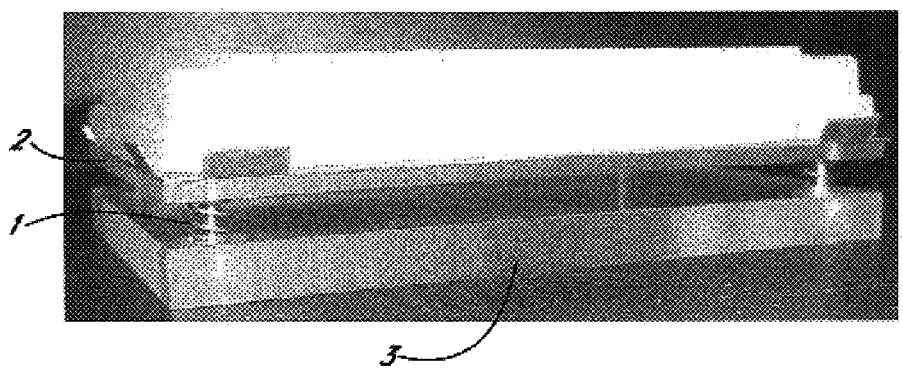
FIG. 4 is an isometric view of the flexible platform of FIGS. 3a and b showing the resistance mechanism, a spring device 1, which is recessed into the base plate 3.
Figure 7A:
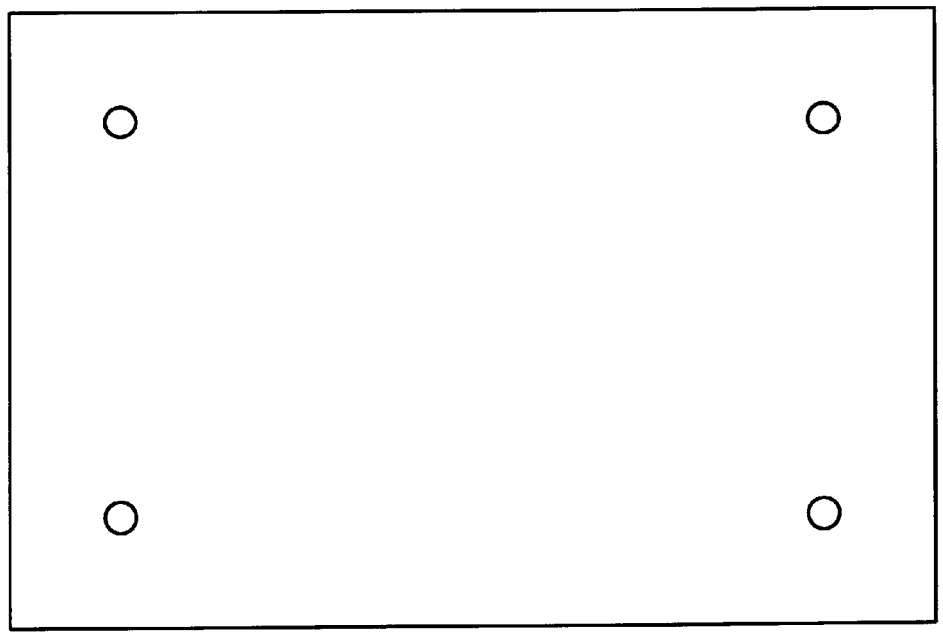
FIGS. 7a and b are an example of a diagram and measurements which could be used in manufacturing a flexible platform of the preferred embodiment.
Figure 7B:
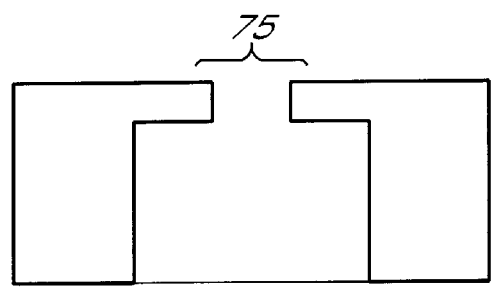

A prototype of the Universal flexible platform was constructed as follows: two plates of acrylic were produced with the following dimensions: The Thick plate—127.76 mm×85.48 mm×9.525 mm (⅜"). The Thin plate—127.76 mm×85.48 mm×about 4.5 mm (0.177"). Each plate had four holes drilled into it as shown in FIG. 7a. Each hole was centered 8 mm from the corner in both the x and y directions. For the thin plate (0.177"), the holes were drilled all of the way through and threaded with a 4/40 thread. For the thick plate (⅜") the holes were drilled 10 mm in diameter, but not all the way through the plate. A one millimeter lip was left. In the center of the lip, a 3.8 mm hole was drilled (see FIG. 7b). This allowed for a recessed spring and pin as shown in FIGS. 3 and 4.

Example 3 provides a method for installation of an embodiment of the flexible platform called the Tender-Touch™ Microplate Holder.

Example 3
TenderTouch™ Microplate Holder for the Biomek® 2000*

A Product comparable to that described in FIGS. 11–16 was produced as in Example 7 and Installation was as follows: Software Setup: In the Bioworks edit module the <Edit> pull-down menu was clicked on, then <Devices . . . > was selected. "Labware Holder" was highlighted in the "Edit Device" pop-up box, and then the <Copy> button was pressed. The following information was entered in the "Device Copy" pop-up box:

| New Name: | TenderTouch |
|---|---|
| Author: | RNAture, Inc. |
| Keyword: | Worksurface |

The <OK> button was pressed and "TenderTouch" was highlighted in the "Edit Device" pop-up box and the <Edit> button pressed. The information in FIG. 1 was entered (below) into the "TenderTouch" pop-up box, and then the <OK> button was pressed. This definition was imported into any Lab Book requiring its use.

The Hardware was Setup as follows: The TenderTouch Microplate Holder was inserted so that the side of the device labeled "FRONT" faced the front of the Biomerk 2000 work surface. The TenderTouch™ was placed into the desired deck location by inserting the detente pins of the device into the orientation holes of the deck. A standard Biomek 2000 (or ORCA®* accessible) labware holder was placed on top of the TenderTouch (the detente pins of the labware holder were inserted into the orientation holes of the TenderTouch™).

When writing a method, the TenderTouch™ was added to the desired location on the deck in the initial configuration. In the method, Labware was placed directly on top of the TenderTouch, and no labware holders were necessary (TenderTouch™ itself represents a modified labware holder).

The TenderTouch™ Microplate Holder allowed for tip-to-well contact and could be used for dispensing low volumes into a microtiter plate (to prevent bubble formation), aspirating low volumes from a microtiter plate (to prevent tip crashes or missed samples), and for complete aspiration of volumes from a microtiter plate (without tip crashes). Regardless of the intended use, one may experiment a little to find the right height when writing a method using TenderTouch™ to access the very bottom of the wells of a microtiter plate. Typically the bottom of the wells will be near the 50% height in the method, but this can depend upon the labware being accessed. In one embodiment, the height was set so that when the pipette tips touched bottom of the plate, the springs on the TenderTouch™ were about halfway compressed. Typically this was at about "35% height". By setting the height to mid-point of the spring compression there is typically about 1.5 mm of z-axis flexibility in both directions. Preferably, the height is not set so low that the top plate of the TenderTouch touches the rubber bumpers of the bottom plate, as this can cause a tip crash.

When using TenderTouch™ for dispensing or aspirating the dispense or aspirate speed was preferably set to 6 or below for optimal performance.

Depending upon the labware holder placed on top of the TenderTouch™ Microplate Holder and the location of fluid within the microtiter plate, the top surface of the TenderTouch may not be completely level. This is not usually a problem, as the TenderTouch™ is specifically designed to overcome these sorts of alignment issues.

Example 4
Aspiration using the TenderTouch™ Microplate Holder

When using the TenderTouch™ Microplate Holder for complete aspiration of larger volumes of liquids, one may notice that some residual fluid is retained on the walls of the microtiter plate. This will vary depending upon the composition of the microtiter plate being used and the composition of the sample/buffer being aspirated. Buffer solutions that have a high affinity for the microtiter plate will achieve the most desirable results (i.e. solutions that "sheet off" the plate will leave less residual on the walls of the wells). Another way to help reduce residual fluid on the walls of the wells is to decrease the aspirate speed below 6.

Example 5
Dispensing using the TenderTouch™ Microplate Holder

When using the TenderTouch™ Microplate Holder for low volume dispensing, it is preferable to ensure that in the "Pipette Transfer" pop-up box, under "Dispense" type, the language "To Deliver" has been selected. If "To Contain" is used, air bubbles may be introduced into the sample.

Example 6
Maintenance of the TenderTouch™ Microplate Holder

Periodically, if a drop in performance is noticed, the springs on the TenderTouch™ may need to be replaced. First, the labware holder is removed from the TenderTouch™, and then the TenderTouch™ is removed from the deck of the Biomek 2000. The location of the small washers located between the spring and the top plate of the TenderTouch™ is noticed. Then, the TenderTouch™ is flipped upside down, and the four shoulder screws are removed with a flat head screwdriver. The two plates are taken apart, and the springs removed. These directions are simply followed in reverse to put the new springs in.

Preferably, the replacement springs furnished by RNAture (catalog #90TT01-1S) are used as any other springs may not give the desired results and can result in damage to the liquid handler.

Example 7
Manufacture of the TenderTouch™

The parts list was as in Table 1.

TABLE 1

| Number | Part | characteristics | Units Needed |
|---|---|---|---|
| 1 | Machined Delrin Top Plate (with heli-coil inserts) | | 1 |
| 2 | Machined Delrin Bottom Plate (with détente pin inserts) | | 1 |
| 3 | Springs | OD = 0.203 inches, ID = 0.173 inches, Free Length = 0.310 inches, Spring Rate = 2.20, Solid Height = 0.120 inches, Wire Diameter = 0.015 | 4 |

TABLE 1-continued

| Number | Part | characteristics | Units Needed |
|---|---|---|---|
|  |  | inches, Total Coils = 7, Material = Music Wire, Closed ends, Gold Irridite Finish |  |
| 4 | Shoulder Screws | 18-8 SS Precision Slotted Shoulder Screw. 125" Shoulder Diameter, 0.313" Shoulder Lg, 4-40 Thread | 4 |
| 5 | Washers | Metric 18-8 Stainless Steel Washer - DIN 125 M2.5 Screw Size, 2.7 mm ID, 6 mm OD, 0.45 mm Thick | 4 |
| 6 | Black Bumpers, adhesive | Adhesive-Backed Polyurethane Bumper Dome Top, ⅜" Diameter, 5/32" Proj, Black | 4 |
| 7 | Top Label (with RNAture Logo) |  | 1 |
| 8 | Side Labels |  | 2 |
| 9 | Front Label |  | 1 |
| 10 | Back Label |  | 1 |

The assembly Directions were as follows:

The Top Plate was identified as the plate with six holes total: four holes in the corners with steel heli-coil inserts, and two open holes. The Top Plate was placed face down on a flat surface in the orientation with the holes (15 see FIG. 10) in the top left and bottom right corners. (If the large, open holes are in the wrong corners, flip the plate over).

Starting with the front left corner hole (with a heli-coil insert), one of the washers was placed on top of the hole so that the hole of the washer was aligned with the hole of the heli-coil.

Now, a spring was placed on top of the washer, aligning the center of the spring with the hole of the washer and the heli-coil.

The Bottom Plate was identified as the plate with only four holes total (one in each corner). On one side of the plate the holes were a larger diameter than the other side of the plate. The top surface of the Bottom Plate is the one with the smaller diameter holes (see FIG. 11).

The Bottom Plate was held with the top surface facing down (large diameter holes facing up), and one shoulder screw was inserted into the front left corner hole, allowing the threaded body of the screw to pass through the smaller diameter hole.

The Bottom Plate was brought close to the Top Plate, and the body of the shoulder screw inserted through the spring, washer, and into the front left corner hole of the Top Plate. Using a flathead screwdriver, the shoulder screw was tightened into the heli-coil of the Top Plate until snug, but not overtightened.

Steps 3 through 7 were repeated for the remaining 3 holes, using the remaining 3 washers, springs, and shoulder screws.

Once assembled, the apparatus was flipped over, so that the top surface of the Top Plate was facing up, and the bottom surface of the Bottom Plate facing down. The apparatus was oriented so that the two open holes of the Top Plate were in the upper right and the lower left.

The Top Label, was located and the backing peeled off and a label placed in the direct center of the Top Plate, with the top of the label facing the back of the device, and the bottom of the label facing the front of the device.

The Side Labels were located and attached looking at the front of the device, by placing one of the Side Labels on the front of the Top Plate, centering right to left and top to bottom. The other labels were applied in the same way.

The device was laid on its side and the distance between the top surface of the Top Plate and the bottom surface of the Bottom Plate was measured with a digital caliper. Preferably, the distance was measured at all four corners and the shoulder screws tightened or loosened to achieve a distance of 22.89 mm at each corner (+/−0.1 mm).

The device was now ready for QC on the Biomek 2000.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. A platform for a liquid-handling robot having at least one robot nozzle for transferring or treating a liquid sample in a sample holder by moving upward and downward, comprising:

a sample platform for receiving the sample holder;

an adapter platform for fitting onto the liquid-handling robot; and a moveable connector elastically connecting the sample platform and the adapter platform, wherein elasticity of the connector is adjusted to be lower than the force of the downward movement of the nozzle to elastically lower the sample platform when the nozzle pushes the sample holder downward, and wherein said moveable connector comprises at least one coil spring and at least one support arranged within or near the coil spring.

2. The platform of claim 1, wherein said support is selected from the group consisting of a screw, a shoulder screw, a pin, a nail, and a rod.

3. The platform of claim 1, further comprising a washer.

4. The platform of claim 1, wherein said moveable connector is selected from the group consisting of: a foam pad, a spring assembly, an air cushion, and a magnet.

5. A platform for a liquid-handling robot having at least one robot nozzle for transferring or treating a liquid sample in a sample holder by moving upward and downward, comprising:
   a sample platform for receiving the sample holder;
   an adapter platform for fitting onto the liquid-handling robot;
   a moveable connector elastically connecting the sample platform and the adapter platform, wherein elasticity of the connector is adjusted to be lower than the force of the downward movement of the nozzle to elastically lower the sample platform when the nozzle pushes the sample holder downward, and at least one adapter pin for positioning the adapter platform in the liquid handling robot.

6. A platform for a liquid-handling robot comprising (i) a detachable sample holder having at least one well or groove for a liquid sample; (ii) an adapter for receiving the platform; and (iii) at least one robot nozzle for transferring or treating the sample in the well by moving upward and downward,
   said platform comprising: (a) an upper surface configured to contact a bottom of the sample holder, (b) a bottom surface configured to contact an upper surface of the adapter, and (c) a mechanism elastically moveable in a direction of movement of the nozzle, wherein elasticity of said platform is adjusted to be lower than the force of the downward movement of the nozzle.

7. The platform of claim 6, wherein the upper surface of the platform is configured to receive a sample holder selected from the group consisting of: a microtiter plate, a PCR plate, a microarray, and a microfluidic plate.

8. The platform of claim 6, wherein the upper surface of the platform is an upper surface of a sample platform, the bottom surface of the platform is a bottom surface of an adapter platform, and the moveable mechanism is constituted between the sample platform and the adapter platform.

9. The platform of claim 8, wherein said moveable mechanism comprises a connector and a spring.

10. The platform of claim 9, wherein said connector is selected from the group consisting of a screw, a pin, a nail, and a rod.

11. The platform of claim 8, further comprising at least one bumper for preventing full compression of the springs.

12. The platform of claim 8, further comprising a helicoil.

13. A method for adapting an automated liquid handler having at least one robot nozzle for transferring or treating a liquid sample in a sample holder by moving upward and downward, comprising attaching a platform comprising:
   a sample platform for receiving the sample holder;
   an adapter platform for fitting onto the automated liquid handler; and
   a moveable connector elastically connecting the sample platform and the adapter platform, wherein elasticity of the connector is adjusted to be lower than the force of the downward movement of the nozzle to elastically lower the sample platform when the nozzle pushes the sample holder downward, to the automated liquid handler to allow for variations in plate and well-size.

14. A method for the complete aspiration of small volumes by an automated liquid handler having at least one robot nozzle for transferring or treating a liquid sample in a sample holder by moving upward and downward, comprising attaching to a liquid plate handler a platform comprising:
   a sample platform for receiving the sample holder;
   an adapter platform for fitting onto the automated liquid handler; and
   a moveable connector elastically connecting the sample platform and the adapter platform, wherein elasticity of the connector is adjusted to be lower than the force of the downward movement of the nozzle to elastically lower the sample platform when the nozzle pushes the sample holder downward.

15. A method for transfer of small volumes by an automated liquid handler having at least one robot nozzle for transferring or treating a liquid sample in a sample holder by moving upward and downward, comprising attaching to a liquid plate handler a platform comprising:
   a sample platform for receiving the sample holder;
   an adapter platform for fitting onto the automated liquid handler; and
   a moveable connector elastically connecting the sample platform and the adapter platform, wherein elasticity of the connector is adjusted to be lower than the force of the downward movement of the nozzle to elastically lower the sample platform when the nozzle pushes the sample holder downward.

16. A method for perfecting the function of microarray spotters having at least one robot nozzle or pin for transferring or treating a liquid sample in a sample holder by moving upward and downward, comprising attaching to an automated liquid handler a platform comprising:
   a sample platform for receiving the sample holder;
   an adapter platform for fitting onto the automated liquid handler; and
   a moveable connector elastically connecting the sample platform and the adapter platform, wherein elasticity of the connector is adjusted to be lower than the force of the downward movement of the nozzle to elastically lower the sample platform when the nozzle pushes the sample holder downward.

17. A platform for any type of liquid handling robot, comprising:
   a sample platform;
   an adaptor platform which fits onto the liquid handling robots; and
   a moveable connector which allows motion on one axis between the two platforms, wherein said movable connector comprises a connector and a spring.

18. The platform of claim 17, wherein said spring is selected from the group consisting of: a standard coiled spring, a conical coiled spring, and a flat spring.

19. The platform of claim 17, wherein said connector is selected from the group consisting of: a screw, a pin a nail, and a rod.

20. The platform of claim 19, wherein said screw is a shoulder screw.

21. The platform of claim 19, wherein said sample platform or said adaptor, or both is manufactured of a material which is inert.

22. A method for adapting liquid plate handlers to allow for variations in plate and well-size, comprising: attaching to a liquid plate handler a platform for any type of liquid handling robot, said platform comprising:
   a sample platform;
   an adaptor platform which fits onto the liquid handling robots; and a moveable connector which allows motion on one axis between the two platforms.

23. A method for the complete aspiration of small volumes by an automated liquid handler, comprising: attaching to an automated liquid handler a platform for any type of liquid handling robot, said platform comprising:

a sample platform;

an adaptor platform which fits onto the liquid handling robots; and a moveable connector which allows motion on one axis between the two platforms.

24. A method for transfer of small volumes by a liquid plate handler, comprising: attaching to an automated liquid handler a platform for any type of liquid handling robot, said platform comprising:

a sample platform;

an adaptor platform which fits onto the liquid handling robot; and a moveable connector which allows motion on one axis between the two platforms.

* * * * *